(12) United States Patent
Ridler et al.

(10) Patent No.: US 11,528,567 B2
(45) Date of Patent: Dec. 13, 2022

(54) SOUND CAPTURE FOCUS ADJUSTMENT FOR HEARING PROSTHESIS

(71) Applicants: Oliver Ridler, Cherrybrook (AU); Martin James Cosenza, Fairfax Station, VA (US)

(72) Inventors: Oliver Ridler, Cherrybrook (AU); Martin James Cosenza, Fairfax Station, VA (US)

(73) Assignee: Cochlear Limited, Macquarie University (AU)

(*) Notice: Subject to any disclaimer, the term of this patent is extended or adjusted under 35 U.S.C. 154(b) by 12 days.

(21) Appl. No.: 16/148,278

(22) Filed: Oct. 1, 2018

(65) Prior Publication Data

US 2019/0037320 A1    Jan. 31, 2019

Related U.S. Application Data

(62) Division of application No. 14/665,722, filed on Mar. 23, 2015, now Pat. No. 10,091,589, which is a division of application No. 13/232,685, filed on Sep. 14, 2011, now Pat. No. 8,989,413.

(51) Int. Cl.
  *H04R 25/00* (2006.01)
  *A61N 1/36* (2006.01)

(52) U.S. Cl.
  CPC ......... *H04R 25/405* (2013.01); *H04R 25/407* (2013.01); *A61N 1/36038* (2017.08); *H04R 2225/023* (2013.01); *H04R 2225/61* (2013.01); *H04R 2225/67* (2013.01); *H04R 2430/20* (2013.01)

(58) Field of Classification Search
  CPC ...... H04R 25/00; H04R 25/55; H04R 25/558; H04R 2225/49; H04R 2460/01
  USPC ................. 381/312–313, 315–317, 320–321
  See application file for complete search history.

(56) References Cited

U.S. PATENT DOCUMENTS

| | | | | |
|---|---|---|---|---|
| 8,391,523 B2* | 3/2013 | Biundo Lotito | ....... | H04R 25/43 381/312 |
| 8,699,719 B2* | 4/2014 | Johnson, Jr. | ........... | H04R 29/00 381/328 |
| 8,737,650 B2* | 5/2014 | Pedersen | .............. | H04R 25/558 381/312 |
| 2007/0127753 A1* | 6/2007 | Feng | ...................... | H04R 1/406 381/313 |
| 2015/0296310 A1* | 10/2015 | Chen | ................. | H04M 1/72591 381/315 |

* cited by examiner

*Primary Examiner* — Suhan Ni
(74) *Attorney, Agent, or Firm* — Piloff Passino & Cosenza LLP; Martin J. Cosenza

(57) ABSTRACT

A hearing prosthesis, the hearing prosthesis including a plurality of sound capture devices and a determinator configured to generate a parameter indicative of an orientation of the plurality of sound capture devices relative to a reference, wherein the hearing prosthesis is configured to adjust a direction of focus of the hearing prosthesis based on at least the parameter.

26 Claims, 10 Drawing Sheets

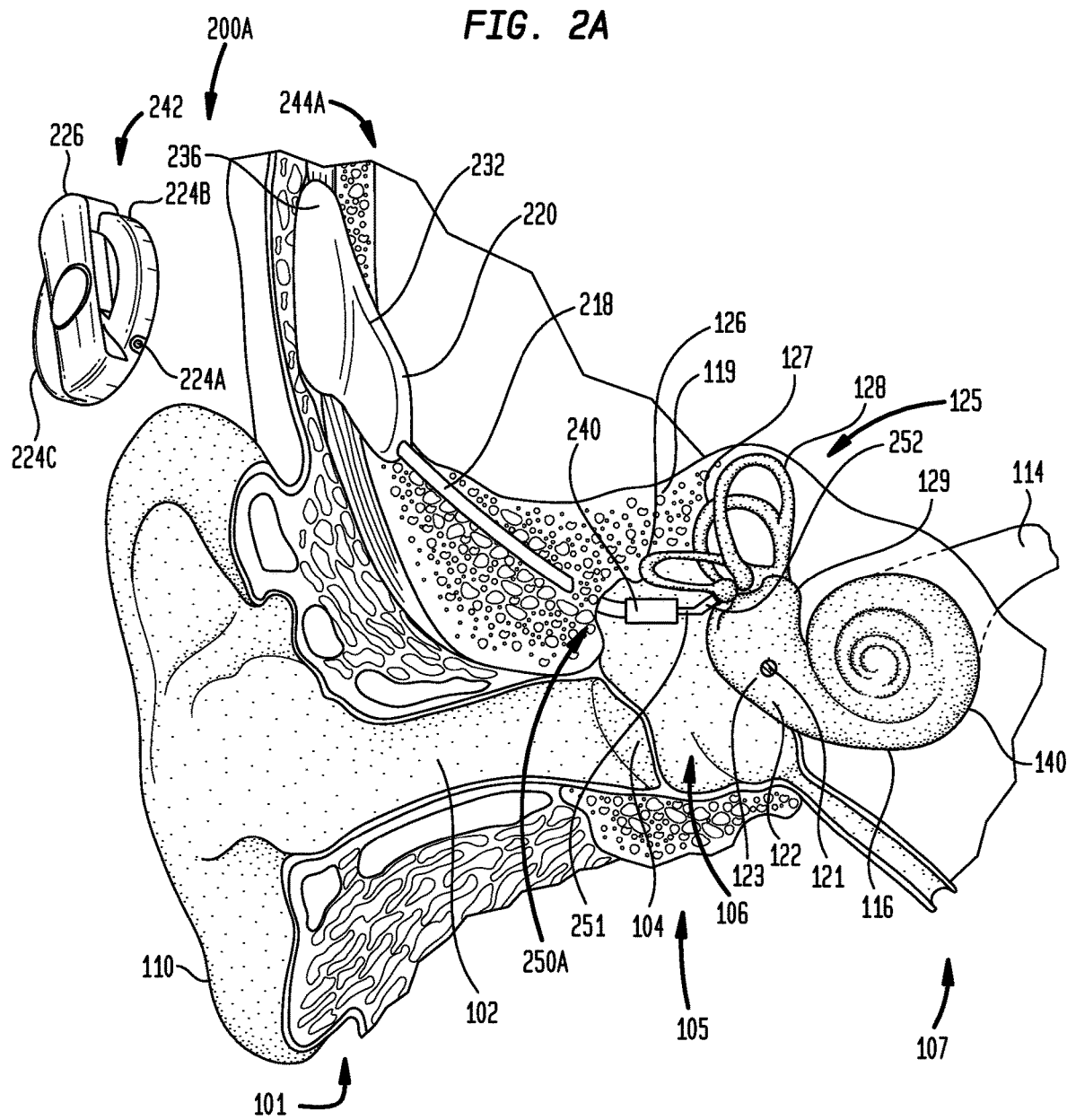

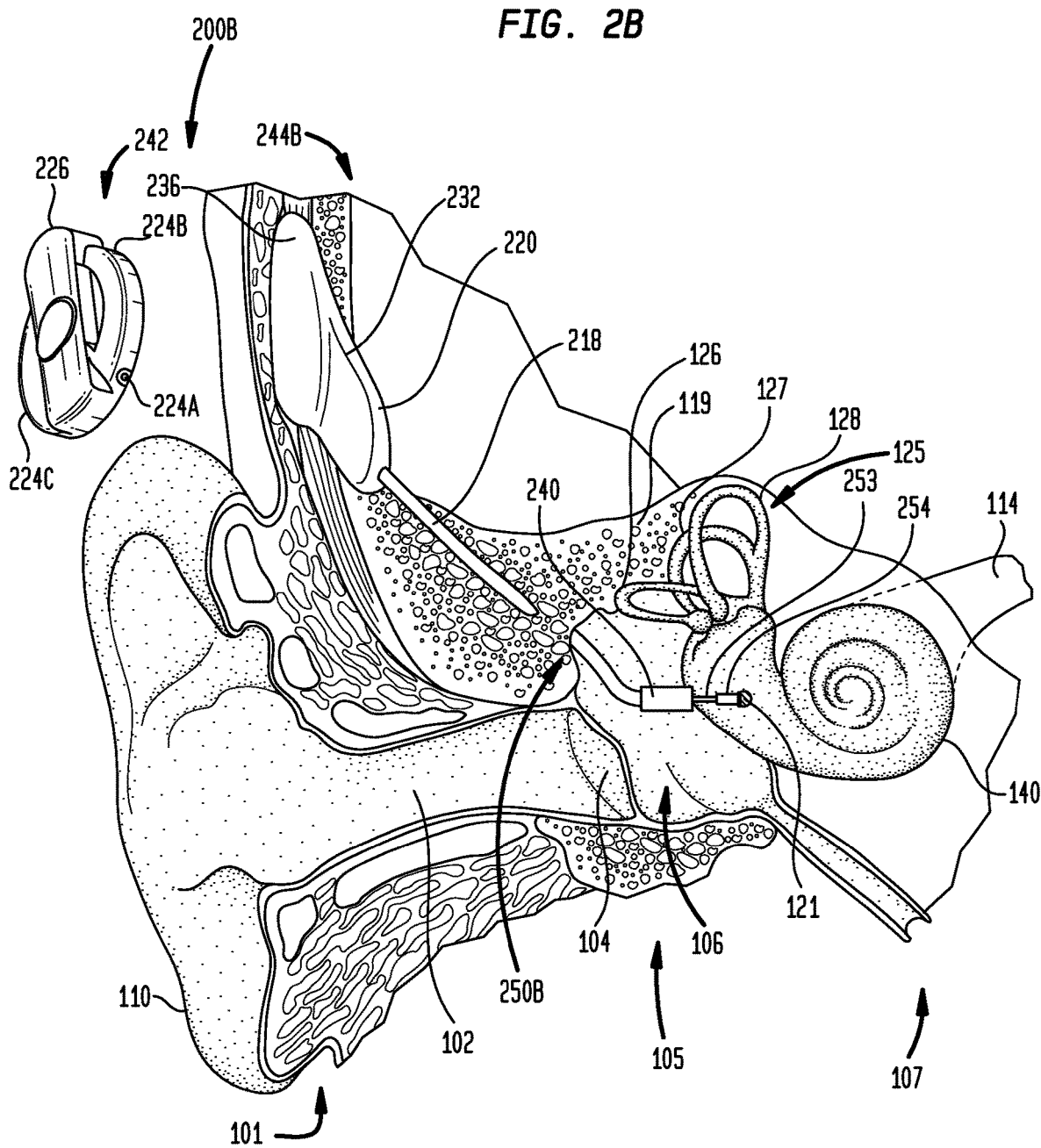

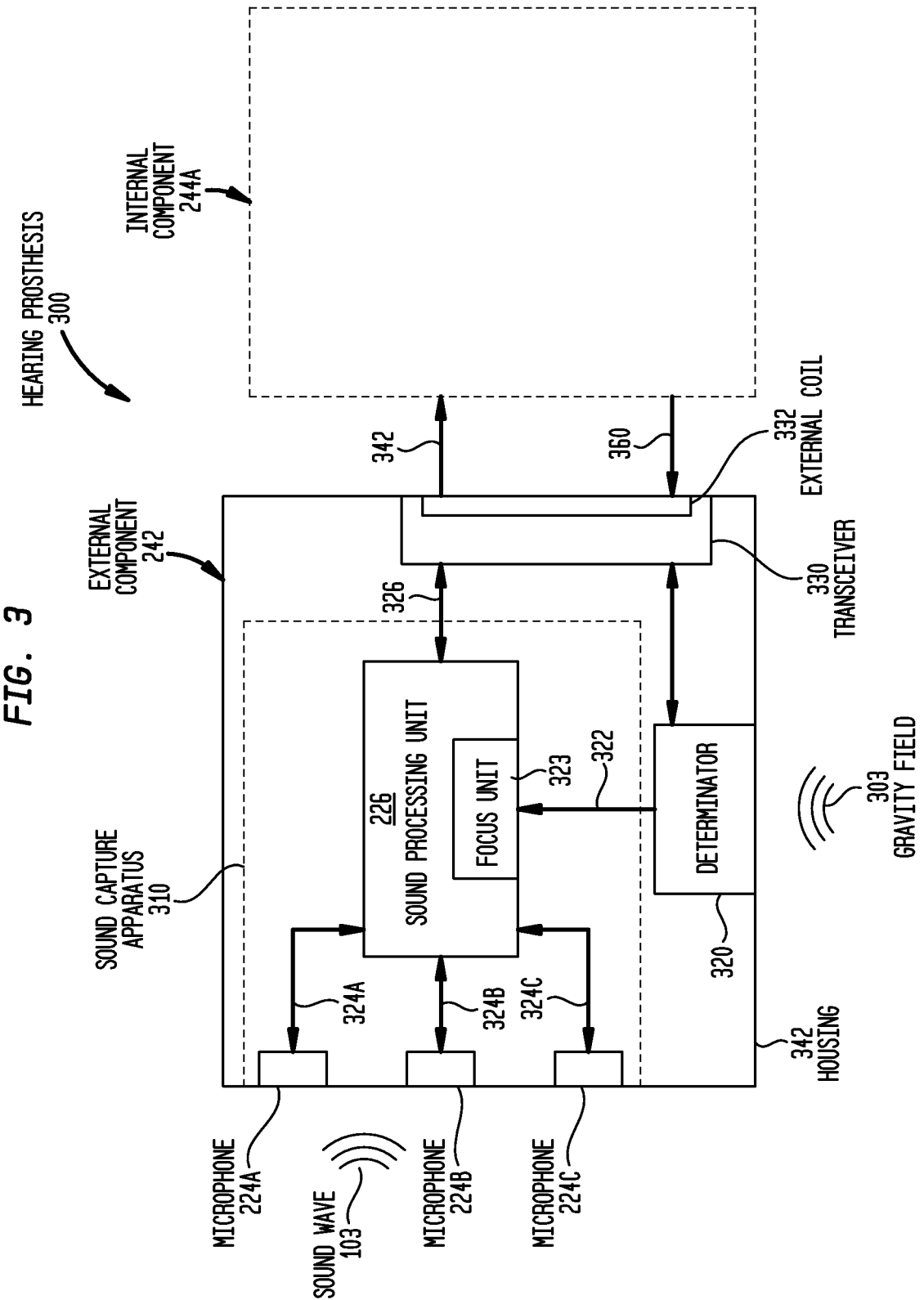

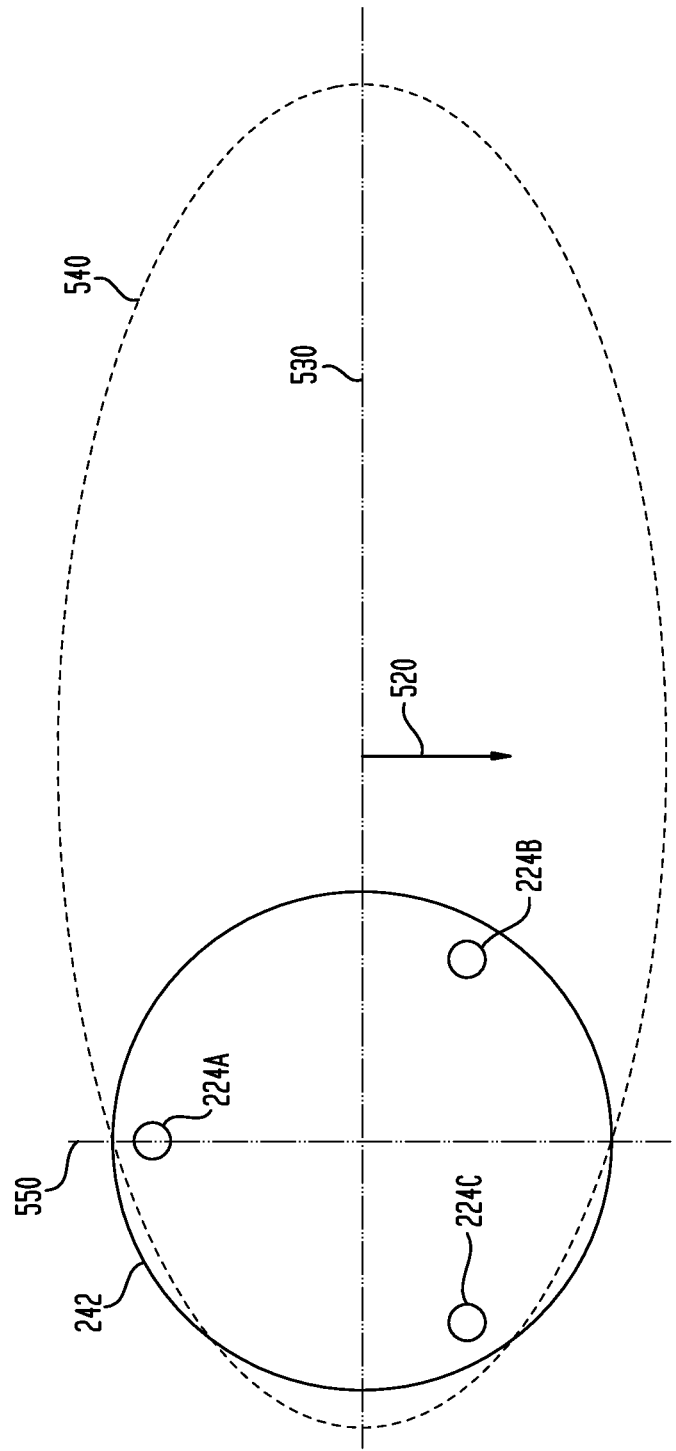

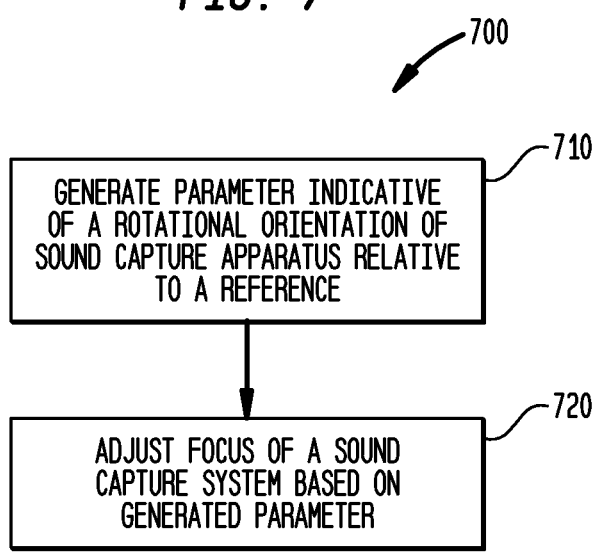

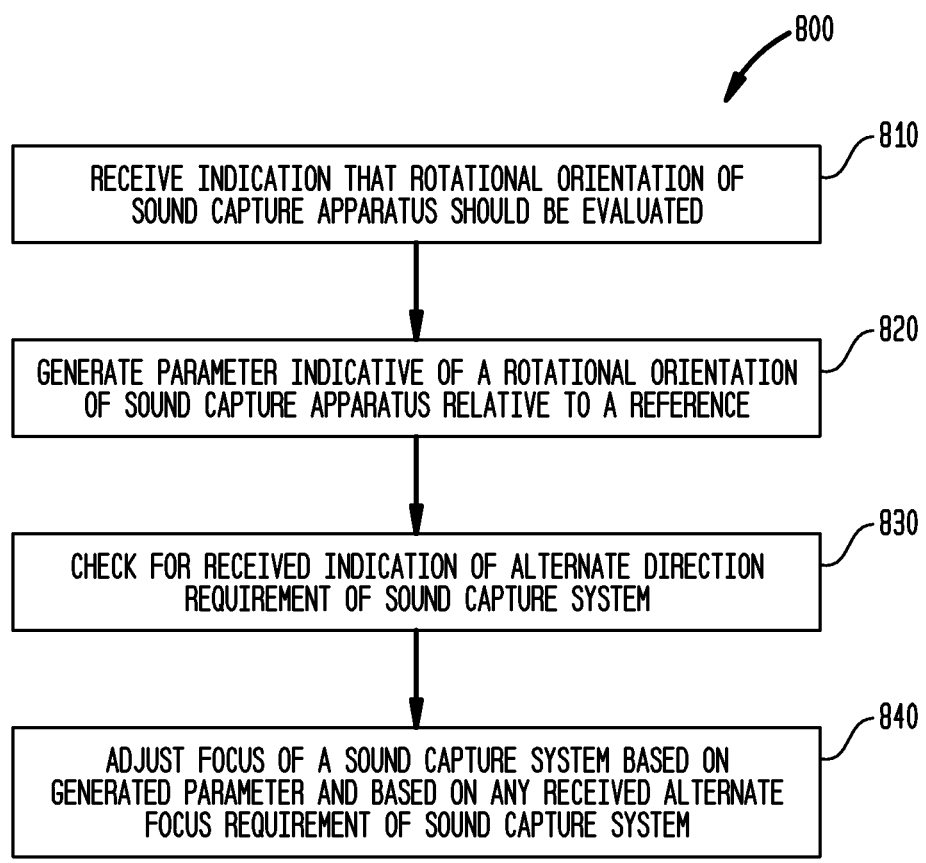

SOUND CAPTURE FOCUS ADJUSTMENT FOR HEARING PROSTHESIS

The present application is a Divisional application of U.S. patent application Ser. No. 14/665,722, filed Mar. 23, 2015, which is a Divisional application of U.S. patent application Ser. No. 13/232,685, filed Sep. 14, 2011 (now U.S. Pat. No. 8,989,413), naming Oliver Ridler as an inventor, the entire contents of that application being incorporated herein by reference in its entirety.

BACKGROUND

Field of the Invention

The present invention relates generally to hearing prostheses, and more particularly, to sound capture focus adjustment for hearing prostheses.

Related Art

Hearing loss, which may be due to many different causes, is generally of two types, conductive and sensorineural. Sensorineural hearing loss is due to the absence or destruction of the hair cells in the cochlea that transduce sound signals into nerve impulses. Various prosthetic hearing implants have been developed to provide individuals who suffer from sensorineural hearing loss with the ability to perceive sound. One such prosthetic hearing implant is referred to as a cochlear implant. Cochlear implants use an electrode array implanted in the cochlea of a recipient to bypass the mechanisms of the ear. More specifically, an electrical stimulus is provided via the electrode array directly to the auditory nerve, thereby causing a hearing sensation.

Conductive hearing loss occurs when the normal mechanical pathways that provide sound to hair cells in the cochlea are impeded, for example, by damage to the ossicular chain or ear canal. However, individuals suffering from conductive hearing loss may retain some form of residual hearing because the hair cells in the cochlea may remain undamaged.

Individuals suffering from conductive hearing loss are typically not candidates for a cochlear implant. Insertion of the electrode assembly into a recipient's cochlea exposes the recipient to potential destruction of the remaining hair cells in the cochlea. Typically, destruction of the cochlea hair cells results in the loss of residual hearing in the portion of the cochlea in which the electrode assembly is implanted.

Rather, individuals suffering from conductive hearing loss typically receive an acoustic hearing aid, referred to as a hearing aid herein. Hearing aids rely on principles of air conduction to transmit acoustic signals to the cochlea. In particular, a hearing aid typically uses an arrangement positioned in the recipient's ear canal or on the outer ear to amplify a sound received at the outer ear of the recipient. This amplified sound reaches the cochlea causing motion of the perilymph and stimulation of the auditory nerve.

Unfortunately, not all individuals who suffer from conductive hearing loss are able to derive suitable benefit from hearing aids. For example, some individuals are prone to chronic inflammation or infection of the ear canal thereby eliminating hearing aids as a potential solution. Other individuals have malformed or absent outer ear and/or ear canals resulting from a birth defect, or as a result of medical conditions such as Treacher Collins syndrome or Microtia. Furthermore, hearing aids are typically unsuitable for individuals who suffer from single-sided deafness (total hearing loss only in one ear). Hearing aids commonly referred to as "cross aids" have been developed for single sided deaf individuals. These devices receive the sound from the deaf side with one hearing aid and present this signal (either via a direct electrical connection or wirelessly) to a hearing aid which is worn on the opposite side. Unfortunately, this requires the recipient to wear two hearing aids. Additionally, in order to prevent acoustic feedback problems, hearing aids generally require that the ear canal be plugged, resulting in unnecessary pressure, discomfort, or other problems such as eczema.

As noted above, hearing aids rely primarily on the principles of air conduction. However, other types of devices commonly referred to as bone conducting hearing aids or bone conduction devices, function by converting a received sound into a mechanical force. This force is transferred through the bones of the skull to the cochlea and causes motion of the cochlea fluid. Hair cells inside the cochlea are responsive to this motion of the cochlea fluid and generate nerve impulses which result in the perception of the received sound. Bone conduction devices have been found suitable to treat a variety of types of hearing loss and may be suitable for individuals who cannot derive sufficient benefit from acoustic hearing aids, cochlear implants, etc, or for individuals who suffer from stuttering problems.

Another type of hearing prosthesis that converts received sound into a mechanical force in treating hearing loss is a direct acoustic cochlear stimulator (also sometimes referred to as a "direct mechanical stimulator" or "inner ear mechanical stimulation device"). A direct acoustic cochlear stimulator comprises an actuator that generates vibrations that are coupled to the inner ear of a recipient and thus bypasses the outer and middle ear.

One other type of hearing prosthesis that converts sound into a mechanical force in treating hearing loss is a middle ear mechanical stimulation device (also sometimes referred to as a "direct drive middle ear hearing device" or "implantable middle ear hearing device"). Such, stimulation devices comprise an actuator that generates vibrations that are coupled to the middle ear of a recipient (e.g., to a bone of the ossicles).

SUMMARY

In one aspect of the present invention, there is provided a hearing prosthesis, the hearing prosthesis comprising a plurality of sound capture devices, and a determinator configured to generate a parameter indicative of an orientation of the plurality of sound capture devices relative to a reference, wherein the hearing prosthesis is configured to adjust a direction of focus of the hearing prosthesis based on at least the parameter.

In another aspect of the present invention, there is provided a method of capturing sound with a hearing prosthesis, comprising automatically focusing a sound capture apparatus based on an orientation of a component of a hearing prosthesis relative to a reference.

In yet another aspect, there is provided an apparatus, comprising a hearing prosthesis including a plurality of sound capture devices configured to automatically direct a sound capture direction in a direction relative to a reference irrespective of a rotational orientation of the sound capture devices relative to the reference.

BRIEF DESCRIPTION OF THE DRAWINGS

Embodiments of the present invention are described below with reference to the attached drawings, in which:

FIG. 2A is a perspective view of an exemplary direct acoustic cochlear stimulator in accordance with embodiments of the present invention;

FIG. 2B is a perspective view of another type of direct acoustic cochlear stimulator in accordance with an embodiment of the present invention;

FIG. 3 is a functional diagram of an exemplary hearing prosthesis in accordance with an embodiment of the present invention;

FIG. 6A is a conceptual diagram depicting orientation of a sound capture system of an exemplary hearing prosthesis in accordance with an embodiment of the present invention;

FIG. 7 presents a flowchart for an exemplary algorithm in accordance with an embodiment of the present invention; and FIG. 8 presents an alternate flowchart for another exemplary algorithm in accordance with an embodiment of the present invention.

DETAILED DESCRIPTION

Embodiments of the present invention are generally directed to a hearing prosthesis that includes an external component attachable to a recipient at a variety of orientations. The external component includes a sound capture apparatus having a plurality of sound capture devices (e.g., microphones) configured to focus on an area relative to the external component (e.g., through beamforming). The sound capture apparatus is configured to adjust a focus of the sound capture apparatus based on the orientation of the sound capture devices relative to a reference, such as a fixed reference (e.g., the direction of gravity). In an exemplary embodiment, this allows the sound capture apparatus to automatically focus on an area in front of the recipient regardless of the rotational orientation of the sound capture devices/external component relative to the recipient.

Figure 1:
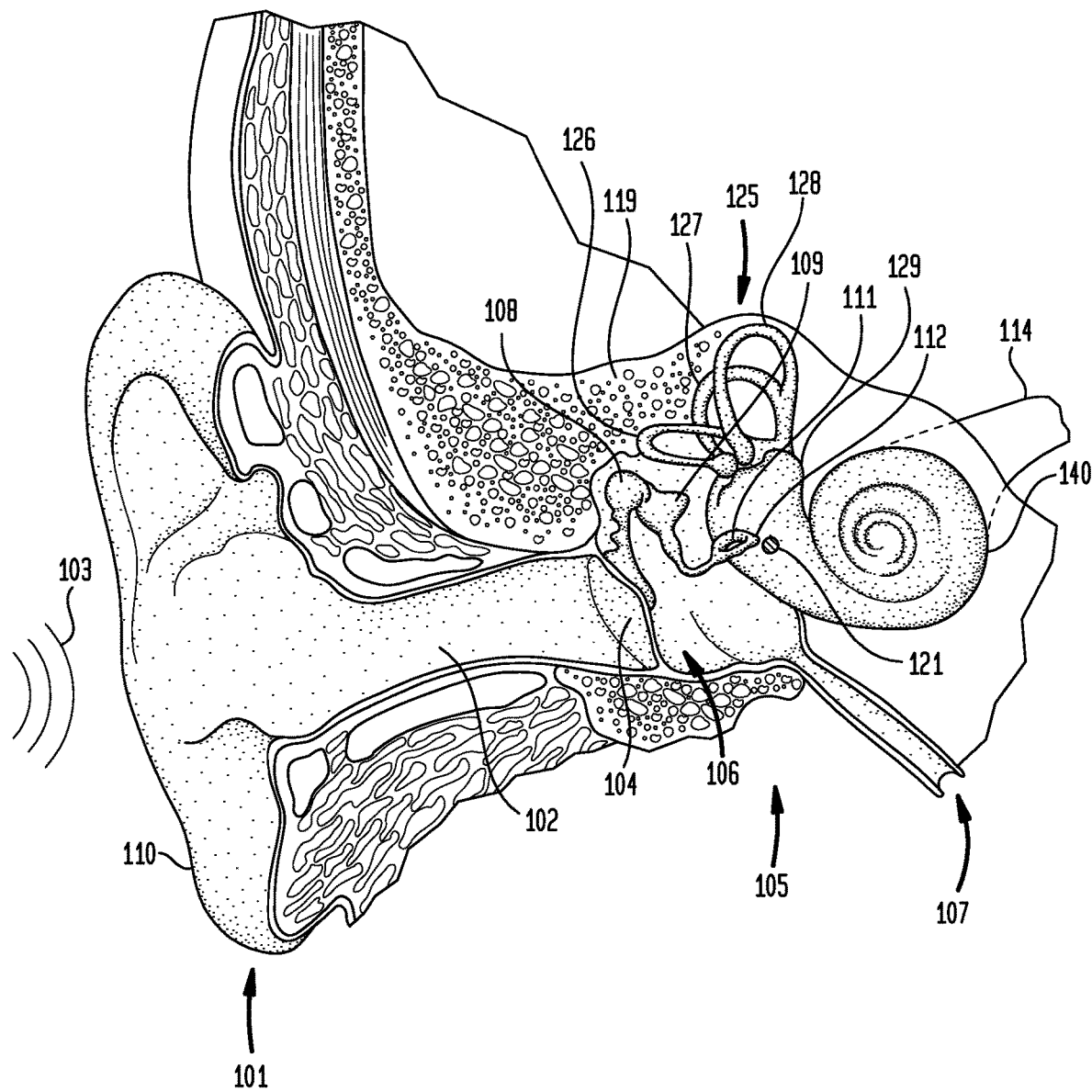
FIG. 1 is perspective view of an individual's head in which an auditory prosthesis in accordance with embodiments of the present invention may be implemented.

FIG. 1 is perspective view of an individual's head in which an auditory prosthesis in accordance with embodiments of the present invention may be implemented. As shown in FIG. 1, the individual's hearing system comprises an outer ear 101, a middle ear 105 and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear cannel 102 is a tympanic membrane 104 which vibrates in response to sound wave 103. This vibration is coupled to oval window or fenestra ovalis 112 through three bones of middle ear 105, collectively referred to as the ossicles 106 and comprising the malleus 108, the incus 109 and the stapes 111. Bones 108, 109 and 111 of middle ear 105 serve to filter and amplify sound wave 103, causing oval window 112 to articulate, or vibrate in response to vibration of tympanic membrane 104. This vibration sets up waves of fluid motion of the perilymph within cochlea 140. Such fluid motion, in turn, activates tiny hair cells (not shown) inside of cochlea 140. Activation of the hair cells causes appropriate nerve impulses to be generated and transferred through the spiral ganglion cells (not shown) and auditory nerve 114 to the brain (also not shown) where they are perceived as sound.

As shown in FIG. 1, semicircular canals 125 are three half-circular, interconnected tubes located adjacent cochlea 140. The three canals are the horizontal semicircular canal 126, the posterior semicircular canal 127, and the superior semicircular canal 128. The canals 126, 127 and 128 are aligned approximately orthogonally to one another. Specifically, horizontal canal 126 is aligned roughly horizontally in the head, while the superior 128 and posterior canals 127 are aligned roughly at a 45 degree angle to a vertical through the center of the individual's head.

Each canal is filled with a fluid called endolymph and contains a motion sensor with tiny hairs (not shown) whose ends are embedded in a gelatinous structure called the cupula (also not shown). As the skull twists in any direction, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements.

FIG. 2A is a perspective view of an exemplary direct acoustic cochlear stimulator 200A in accordance with embodiments of the present invention.

Direct acoustic cochlear stimulator 200A comprises an external component 242 that is directly or indirectly attached to the body of the recipient, and an internal component 244A that is temporarily or permanently implanted in the recipient. External component 242 typically comprises two or more sound input elements, such as microphones 224A, 224B, and 224C for detecting sound, a sound processing unit 226, a power source (not shown), and an external transmitter unit (also not shown). The external transmitter unit is disposed on the exterior surface of sound processing unit 226 and comprises an external coil (not shown). Sound processing unit 226 processes the output of microphones 224 and generates encoded signals, sometimes referred to herein as encoded data signals, which are provided to the external transmitter unit. For ease of illustration, sound processing unit 226 is shown detached from the recipient.

In the present embodiment, microphones 224A, 224B, and 224C are configured as a microphone array, where sound processing unit 226 processes the signals received from the microphones 224A, 224B, and 224C to effect a microphone beam shape. For example, in an embodiment, the sound processing unit processes the signals received from microphones 224 to form microphone beam shape pointed towards the front of the recipient. A further description of exemplary beam shapes will be discussed below. Although microphones 224 are illustrated as dispersed around the edges of external component 242, in other embodiments the microphones 224 may be distributed in differmt configurations. For example, microphones 224 may be distributed on the outward facing face of external component 242. Additionally, in other embodiments the number of microphones 224 may be any number of two or more microphones that may be used for effecting a beam shape in particular direction.

Internal component 244A comprises an internal receiver unit 232, a stimulator unit 220, and a stimulation arrangement 250A. Internal receiver unit 232 and stimulator unit 220 are hermetically sealed within a biocompatible housing, sometimes collectively referred to herein as a stimulator/receiver unit.

Internal receiver unit 232 comprises an internal coil (not shown), and preferably, a magnet (also not shown) fixed relative to the internal coil. The external coil transmits electrical signals (i.e., power and stimulation data) to the internal coil via a radio frequency (RF) link. The internal coil is typically a wire antenna coil comprised of multiple turns of electrically insulated single-strand or multi-strand platinum or gold wire. The electrical insulation of the internal coil is provided by a flexible silicone molding (not shown). In use, implantable receiver unit 132 is positioned in a recess of the temporal bone adjacent auricle 110 of the recipient in the illustrated embodiment.

In the illustrative embodiment, stimulation arrangement 250A is implanted in middle ear 105. For ease of illustration, ossicles 106 have been omitted from FIG. 2A. However, it should be appreciated that stimulation arrangement 250A is implanted without disturbing ossicles 106 in the illustrated embodiment.

Stimulation arrangement 250A comprises an actuator 240, a stapes prosthesis 252 and a coupling element 251. In this embodiment, stimulation arrangement 250A is implanted and/or configured such that a portion of stapes prosthesis 252 abuts an opening in one of the semicircular canals 125. For example, in the illustrative embodiment, stapes prosthesis 252 abuts an opening in horizontal semicircular canal 126. It would be appreciated that in alternative embodiments, stimulation arrangement 250A is implanted such that stapes prosthesis 252 abuts an opening in posterior semicircular canal 127 or superior semicircular canal 128.

As noted above, a sound signal is received by two or more microphones 224, processed by sound processing unit 226, and transmitted as encoded data signals to internal receiver 232. Based on these received signals, stimulator unit 220 generates drive signals which cause actuation of actuator 240. This actuation is transferred to stapes prosthesis 252 such that a wave of fluid motion is generated in horizontal semicircular canal 126. Because, vestibule 129 provides fluid communication between the semicircular canals 125 and the median canal, the wave of fluid motion continues into median canal, thereby activating the hair cells of the organ of *Corti*. Activation of the hair cells causes appropriate nerve impulses to be generated and transferred through the spiral ganglion cells (not shown) and auditory nerve 114 to the brain (also not shown) where they are perceived as sound.

FIG. 2B is a perspective view of another type of direct acoustic cochlear stimulator 200B in accordance with an embodiment of the present invention. Direct acoustic cochlear stimulator 200B comprises an external component 242, which is directly or indirectly attached to the body of the recipient, and an internal component 244B which is temporarily or permanently implanted in the recipient. As described above with reference to FIG. 2A, external component 242 typically comprises two or more sound input elements, such as microphones 224A, 224B, and 224C, a sound processing unit 226, a power source (not shown), and an external transmitter unit (also not shown). Also as described above, internal component 244B comprises an internal receiver unit 232, a stimulator unit 220, and a stimulation arrangement 250B.

In the illustrative embodiment, stimulation arrangement 250B is implanted in middle ear 105. For ease of illustration, ossicles 106 have been omitted from FIG. 2B. However, it should be appreciated that stimulation arrangement 250B is implanted without disturbing ossicles 106 in the illustrated embodiment.

Stimulation arrangement 250B comprises an actuator 240, a stapes prosthesis 254 and a coupling element 253 connecting the actuator to the stapes prosthesis. In this embodiment stimulation arrangement 250B is implanted and/or configured such that a portion of stapes prosthesis 254 abuts round window 121.

As noted above, a sound signal is received by two or more microphones 224, processed by sound processing unit 226, and transmitted as encoded data signals to internal receiver 232. Based on these received signals, stimulator unit 220 generates drive signals which cause actuation of actuator 240. This actuation is transferred to stapes prosthesis 254 such that a wave of fluid motion is generated in the perilymph in scala tympani. Such fluid motion, in turn, activates the hair cells of the organ of *Corti*. Activation of the hair cells causes appropriate nerve impulses to be generated and transferred through the spiral ganglion cells (not shown) and auditory nerve 114 to the brain (also not shown) where they are perceived as sound.

It should be noted that the embodiments of FIGS. 2A and 2B are but two exemplary embodiments of a direct acoustic cochlear stimulator, and in other embodiments other types of direct acoustic cochlear stimulator are implemented. Further, although FIGS. 2A and 2B provide illustrative examples of a direct acoustic cochlear stimulator system, in other embodiments a middle ear mechanical stimulation device can be configured in a similar manner, with the exception that instead of the actuator 240 being coupled to the inner ear of the recipient, the actuator is coupled to the middle ear of the recipient. For example, in an embodiment, the actuator stimulates the middle ear by direct mechanical coupling via coupling element to ossicles 106 (FIG. 1), such to incus 109 (FIG. 1).

In determining the drive signals to cause actuation of actuator 240, the resonance peak of the actuator are taken into account by the stimulator unit 220 in the presently described embodiment. As is known to one of skill in the art, resonance refers to the tendency of a system to oscillate with a larger amplitude at some frequencies than at others. And, a resonance peak refers to frequencies at which a peak in the amplitude occurs.

It is noted that while the above embodiment has been described in terms of a direct acoustic cochlear stimulator system, other embodiments of the present invention may be practiced with other types of hearing prostheses, such as a cochlear implant and/or a bone conduction device and/or a combination of the devices/systems detailed herein. In some embodiments, any hearing prosthesis that utilizes an external component that has a sound capture apparatus configured to focus on an area (i.e., having directional/directionality capability) that may be attached to a recipient in a variety of orientations may be practiced with some embodiments of the present invention.

Figure 4:
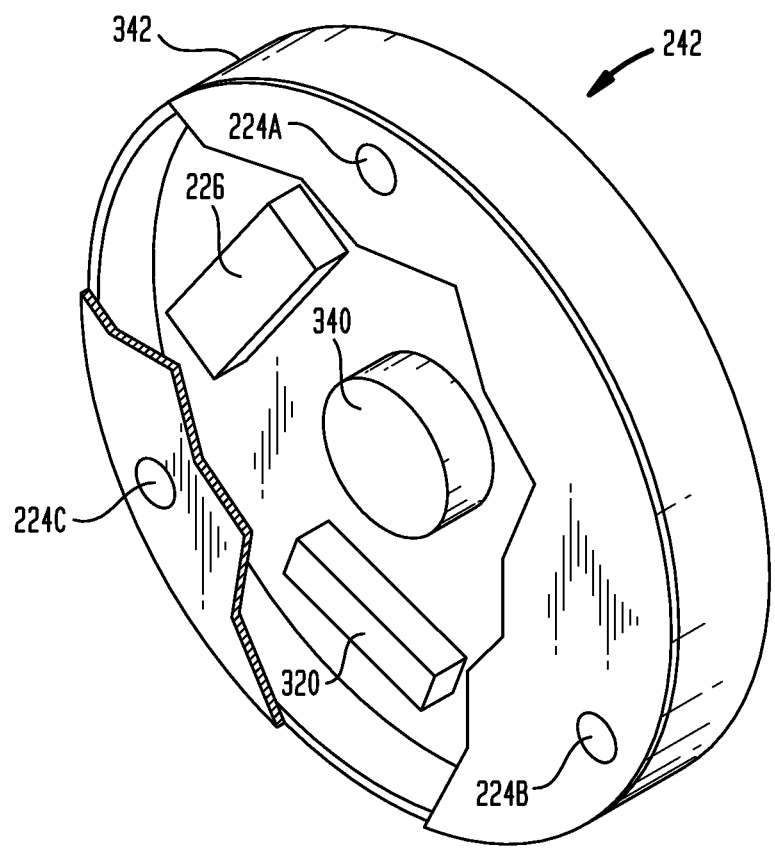
FIG. 4 is a perspective view of an external component of an exemplary hearing prosthesis in accordance with an embodiment of the present invention.

FIG. 3 depicts a functional block diagram of a hearing prosthesis 300 according to an exemplary embodiment of the present invention, and FIG. 4 depicts an isometric view of an exemplary external component 242 of the exemplary hearing prosthesis 300. In an exemplary embodiment, the hearing prosthesis 300 may correspond to the direct acoustic cochlear stimulator 200A detailed above, with external component 242 corresponding to the external component 242 detailed above with respect to FIGS. 2A and 2B and internal component 244A corresponding to the internal component 244A detailed above with respect to FIGS. 2A and 2B. FIG.

In the exemplary embodiment of FIGS. 3 and 4, the external component 242 includes microphones 224A, 224B and 224C that are in signal communication with sound processing unit 226 via signal routes 324A, 324B and 324C. Collectively, these components form a sound capture apparatus 310. As will be detailed below, the sound capture apparatus may also include a focus unit 323 that is part of the sound processing unit 226, but may also be a separate component from the sound processing unit 226. The sound processing unit 226 is in signal communication with transceiver 330, which includes a coil 332 (corresponding to the external coil referenced above with respect to FIGS. 2A and 2B). Sound processing unit 226 outputs signals indicative of processed captured sound via signal route 326 to transceiver 330, which transmits via external coil 332 an electromagnetic signal 342 to the internal component 244A. External component 242 also includes a determinator 320 which functions to determine the orientation of the external device and/or the sound capture apparatus and, in an exemplary embodiment, is sensitive to a gravity field 303, and a magnet 340. The sound capture apparatus 310 and the determinator 320 collectively form a sound capture system. These components will be described further below. Also, in an exemplary embodiment, the sound processing unit 226 may be located in the internal component 244A of the hearing prosthesis 300, as will be described below.

While the embodiment of FIGS. 3 and 4 utilizes three sound capture devices in the form of three respective microphones, other embodiments may use more than three sound capture devices/microphones. In the embodiment of FIGS. 3 and 4, the microphones are arrayed on the front face of the housing 342 at about 120 degree intervals (e.g., at the 12 o'clock, 4 o'clock and 8 o'clock position). However, in other embodiments, the microphones may be arrayed about the side of the housing 342 as depicted above in FIG. 2A. Microphones on the side and the front may be used in combination. Moreover, the spacing of the microphones may be different than that of FIGS. 3 and 4. For example, the microphone pattern may be a first microphone located at the 12 o'clock position, a second microphone located at the 3 o'clock position, and a third microphone located at the 7 o'clock position. Any spatial arrangement of three or more microphones may be used in some embodiments of the present invention if such spatial arrangement will permit such embodiments to be practiced.

Figure 5:
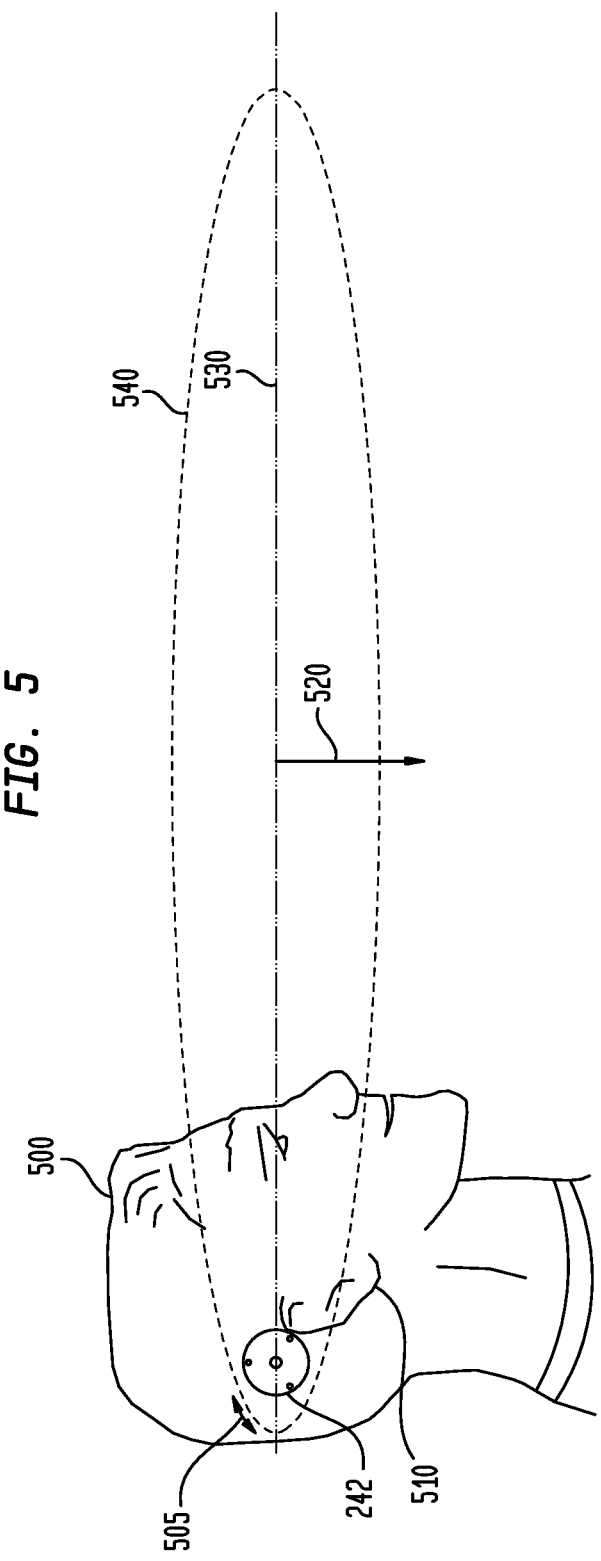
FIG. 5 is a side view of an external component of an exemplary hearing prosthesis attached to a recipient in accordance with an embodiment of the present invention.

As may be seen in FIGS. 3 and 4, the external coil 332 of transceiver 330, the sound processing unit 226 and the microphones 224A, 224B and 224C are packaged in a single unit within or otherwise on a housing 342. (In an exemplary embodiment, as noted above, the sound processing unit 226 may be located elsewhere.) Such a device is sometimes referred to as a coil sound processor, a coil microphone and/or a button processor/sound processor, etc., because the external coil that is used to communicate with the internal component 244A is housed within or otherwise supported by the same components that house or support the sound processor unit and/or the microphones. This is in contrast to an external component of a hearing prosthesis in which the microphone(s) and/or sound processor unit are housed in or otherwise located on a so-called behind-the-ear (BTE) unit that hooks around the ear and is in signal communication with an external coil remote from the housing of the BTE unit. In this regard, the external component 242 according to an embodiment of the present invention is a device that is attachable to the head of a recipient without contacting the recipient's ear and/or otherwise being significantly supported by the recipients' ear or other appendage of the recipient. In an embodiment, the external component 242 is attachable to the head of the recipient such that a face of the external component 242 (opposite side of that which may be seen in FIG. 4) abuts the skin of the recipient and there is no contact and/or minimal contact with skin of the recipient by the sides of the external component 242. FIG. 5 depicts such an exemplary external component 242 so attached to a recipient 500 having an ear 510. (Additional aspects of FIG. 5 will be described below.)

In an exemplary embodiment of the present invention, the external component 242 is held against the head of a recipient by a magnetic field that is established between the external component 242 and the internal component 244A. As noted above, the external component 242 may include magnet 340 and/or other ferromagnetic material fixed relative to the external coil 332 and/or the internal component may include a magnet (not shown) fixed relative to the internal coil (not shown). The magnetic field may be established between these magnet(s) to hold the external component 242 against the head of the recipient 500 such that the radio frequency (RF) link between the two components can be maintained (e.g., the respective coils are sufficiently aligned with one another and sufficiently in close proximity to one another).

As will be readily apparent from the above, in at least some embodiments of the external component 242, the external component 242, and thus the sound capture apparatus 310 (and, more particularly, the microphones 224A, 224B and 224C) may be placed on the recipient in two or more of any number of rotational orientations relative to the recipient. (It is noted that as described herein, the orientation of the external component 242 will be considered fixed relative to the orientation of the sound capture apparatus 310 (and, more particularly, the microphones 224A, 224B and 224C), and visa-versa, and reference herein to the orientation of one will be considered reference to the orientation of the other, and visa-versa, unless otherwise noted.)

Figure 6B:
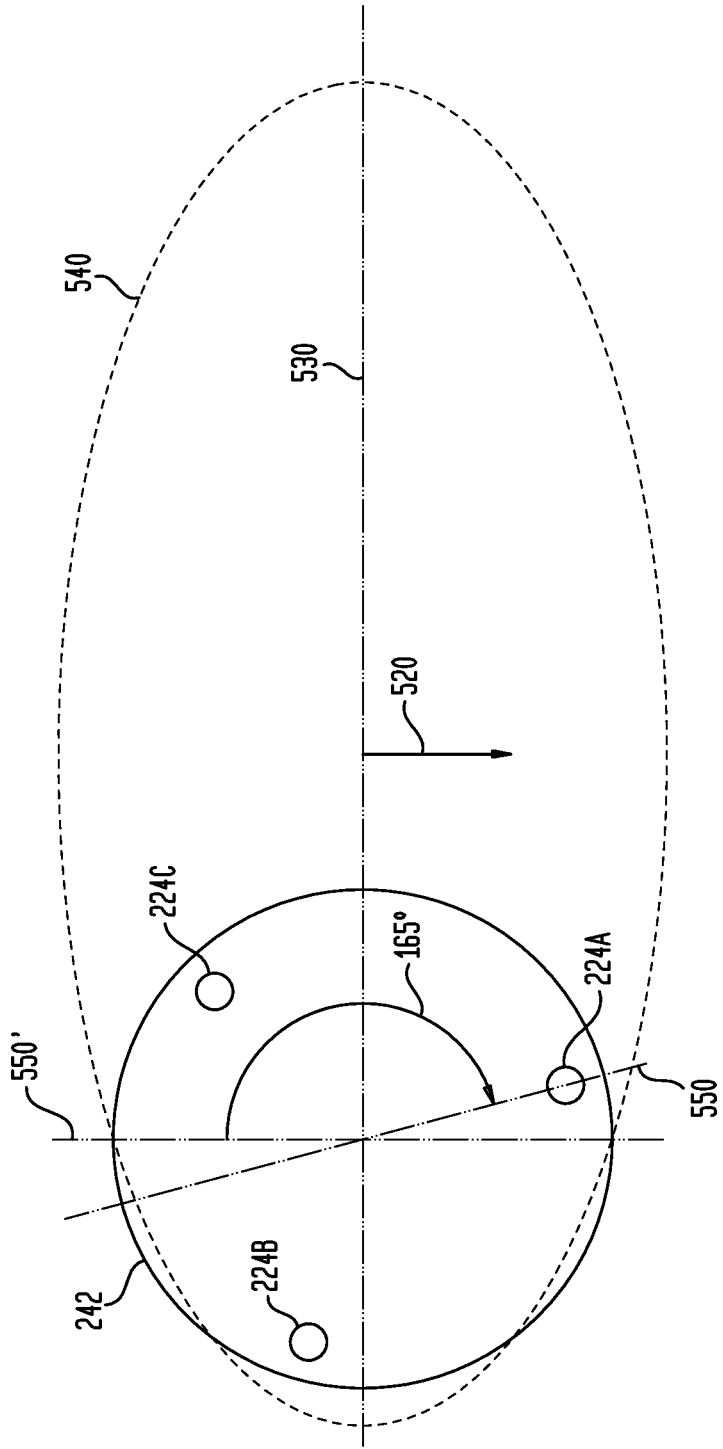
FIG. 6B is a conceptual diagram depicting adjusted orientation, relative to that depicted in FIG. 6A, of the sound capture system of an exemplary hearing prosthesis in accordance with an embodiment of the present invention.

Briefly, FIGS. 6A and 6B depict two different placements of the external component 242 having two different rotational orientations relative to the recipient, where the orientation of the external component 242 in FIG. 6B corresponds to a rotation of about 165 degrees clockwise from that of FIG. 6A. As may be seen, the orientation of microphones 224A, 224B and 224C relative to the horizontal line 530 are different between the two figures. These figures will be further described below.

The external component 242 of FIG. 4 contrasts with an external component utilizing a BTE unit, which typically has the feature that the microphone(s) of the external component face in about the same direction every time the recipient attaches the external component to himself or herself. This is because the housing of the BTE unit conforms to the recipient's ear and thus any component fixedly mounted to the housing, such as the microphones, will be located relative to the recipient in about the same orientation every time. Conversely, the rotational freedom of the external component 242 of the present invention exists because, in at least some embodiments, the magnetic field between the external component 242 and the internal component 244A simply pulls the external component 242 towards the internal component, and there is no portion of the recipient that indexes the external component 242 to a specific rotational orientation (in contrast to a BTE unit vis-à-vis the ear). Also, the magnetic field does not index the external component. Moreover, after attachment to the recipient, the external component 242 may rotate relative to the recipient. While friction between the skin and/or hair of the recipient and the external component 242 tends to react against at least limited rotational forces imparted onto the external component 242 after it is attached to the head of the recipient, the rotational orientation of the external component 242 may still change after attachment.

A result of the fact that the external component 242 may be held on the recipient in a variety of rotational orientations and/or that the rotational orientation of the external component 242 may change after attachment to the recipient is that (i) the orientation of the microphones 224A, 224B and 224C vis-à-vis the area in front of the recipient may be different each time that the recipient attaches the external component 242 to himself or herself and/or (ii) the orientation of the microphones vis-à-vis the area in front of the recipient may change after attachment. In this regard, an exemplary embodiment of the present invention includes a sound capture apparatus/sound capture system that is configured to focus on an area. As will be detailed further below, such focusing capability/directional capability may be achieved via beamforming, where the beamforming is achieved via signal processing to achieve spatial selectivity of the sound capture apparatus.

The directional capability/focusing capability of the sound apparatus 310/sound capture system has utility in embodiments where it can be correlated to a specific area relative to the recipient. A sound capture apparatus configured to focus on an area, such as an area relative to the external component 242, permits the sound capture apparatus/sound capture system to be "focused" in a given direction so that sound originating or otherwise traveling from that direction is weighted relative to other sounds, thereby permitting the recipient to hear more of that sound than other sounds. Such a feature has utility in that users of hearing prostheses often seek to hear words spoken to them to the exclusion of other words spoken to others, and thus the sound capture apparatus 310 can be focused to better capture such spoken sounds. Specifically, because a user typically faces the direction from which the spoken words originate or otherwise travel from, an embodiment of the present invention permits the sound capture apparatus to focus in a specific direction relative to the external component 242 to better capture sound from that specific direction. Because, as noted above, the external component 242 may be held on the user in a variety of orientations, an embodiment of the present invention permits the focus of the sound capture apparatus to be adjusted based on a parameter indicative of the rotational orientation of the external component 242 relative to a reference, such as a fixed reference. (Hereinafter, the reference will generally be described in terms of a fixed reference.) In an exemplary embodiment, the determinator 320 of the external component 242 provides this parameter indicative of the rotational orientation of the external component 242, as will be described further below.

FIG. 7 provides a flow-chart 700 representing an algorithm that may be used in an exemplary embodiment of the present invention. In an exemplary embodiment, a controller, which may be included in the signal processing unit 226, which may be the signal processing unit 226, which may be the focus unit 323, or which may be a separate unit, may be configured to execute such an algorithm (i.e., control the various components of the external component 242 execute this algorithm). In the exemplary algorithm, at step 710, a parameter indicative of a rotational orientation of the external component 242 and/or the sound capture apparatus 310 and/or the microphones 224A, 224B and 224C, relative to a reference, such as a fixed reference, is generated. At step 720, the focus of the sound capture apparatus 320 is adjusted based on the generated parameter generated in step 710. The ramifications of this algorithm will now be described with respect to FIGS. 5, 6A and 6B.

As noted above, FIG. 5 depicts the external component 242 attached to a recipient 500. As noted above, the rotational orientation of the external component 242 and/or the sound capture apparatus 310 may be different each time that the external component 242 is attached to the recipient, as is represented by arrows 505 in FIG. 5. In FIG. 5, arrow 520 reflects the direction of gravity relative to the recipient 500 as depicted when the recipient is standing erect and his or her head is not tilted upward or downward. A line 530 normal to the direction of gravity that passes through the geometric center of the external component 242 has been added to FIG. 5 for ease of explanation. FIG. 6A duplicates some of the images depicted in FIG. 5 where the orientation of the images presented in FIG. 6A are identical to those depicted in FIG. 5. As may be seen, the rotational orientation of the external component 242 and/or the sound capture apparatus 310 is such that microphone 224A is located at the 12 o'clock position. In FIG. 6A, a line 550 has been drawn extending through the 12 and 6 o'clock positions is parallel to the direction of gravity 520, this line being a reference line as further detailed below.

As noted above, the external component 242 is configured to adjust a focus of the sound capture apparatus 310. Some exemplary embodiments of such a configuration will now be described. It is noted herein that a sub-component described as having a given capability also means that a component including that sub-component has that capability.

In an exemplary embodiment, referring to FIG. 3, the external component 242 includes a focus unit 323 that is configured to adjust the direction of focus of the sound capture apparatus 310. As depicted in FIG. 3, the focus unit 323 is part of sound processing unit 226. In some embodiments, the focus unit 323 may be a separate component from the sound processing unit 226 that is in signal communication therewith via a communication line. In some embodiments, the determinator 320 communicates with the focus unit 323 (directly or indirectly). Hereinafter, the functionality of the focus unit 323 may be applied to the sound processor 226, and reference may be made to the sound processor 226 having the functionality of the focus unit. Moreover, the functionality of the focus unit 323 may be applied to the external component 242 and to the hearing prosthesis 300, and reference may be made to the external component 242 and the hearing prosthesis 300 as having the functionality of the focus unit 323.

In an exemplary embodiment, the adjustment made by the focus unit 323 is made to adjust the focus (i.e., directionality) of the sound capture apparatus 310 such that the sound capture apparatus 310 focuses on the area in front of the recipient. However, as noted above, the external component 242, and thus the microphones 224A, 224B and 224C, may be placed on the recipient such that it has/they have a variety of rotational orientations. Accordingly, in an exemplary embodiment, the hearing prosthesis 300 utilizes the direction of gravity 520, which it detects utilizing determinator 320, to direct the sound capture apparatus 310 such that it focuses on an area in front of the recipient. Specifically, in an exemplary embodiment, the focus unit 323 is configured to adjust the focus of the sound capture apparatus 310 to focus on an area that is aligned with a direction normal (or, in an alternate embodiment, at another desirable angle, as will be described below) to the direction of gravity 520 and to the right of the external component 242 (with reference to the external component 242 as depicted in FIGS. 5, 6A and 6B, corresponding to a location in front of the recipient 500) when the external component is attached to the right side of a recipient's head (or to the left of the external component, with respect to FIGS. 5, 6A and 6B, also corresponding to the front of the recipient 500 when the external component is attached to the left side of the recipient's head). Such adjustment will typically focus on the area in front of the recipient during normal use of the external component 242. (An embodiment that accounts for the possibility that the recipient's head may not be consistently aligned with the direction of gravity is discussed below.)

Element 540 of the figures depicts a conceptual sound focus lobe representing an area on which the sound capture apparatus 310 is focused. (Note that this is a conceptual depiction of a sound focus lobe.) As may be seen, focused area 540 is an area that extends normal to the direction of gravity 520 in front of the recipient with a centerline 530 at about head level of the recipient. The external component 242 may be configured to automatically focus the beam in a given direction once the direction of gravity 520 is determined. This may be done utilizing software, hardware and/or firmware based on the fact that, in some embodiments, the external component 242 may be attached to the same side of the recipient in that the implantable component 244A is located only on one side of the recipient (indeed, it is typically attached at the same location). This further may be done utilizing software, hardware and/or firmware based on the fact that, in some embodiments, the external component 242 may be attached at locations on two sides of the recipient in that the recipient may have two implantable components 244A located on both sides of the recipient. The software, hardware and/or firmware may be configured to automatically determine which side of the head the external component 242 is attached, and focus accordingly. In other embodiments, the external component 242 may receive input from the recipient in this regard, and, using the determined direction of gravity 520, focus the sound capture apparatus 310 accordingly. Thus, an embodiment of the present invention provides a device, system and method that permits the orientation of the sound capture apparatus 310, relative to the recipient, to be variable, while maintaining a focus of the sound capture apparatus 310 towards an area in front of the recipient 500, by determining a parameter indicative of the rotational orientation of the external component 242 relative to a fixed reference. As noted above, some embodiments utilize beamforming. In this regard, an exemplary embodiment includes automatically directing a sound capture direction in a desired direction through beamforming.

More specifically, with reference to FIGS. 3 and 4 above, determinator 320, which may be an accelerometer fixedly held in the external component 242, generates a parameter indicative of the rotational orientation of the external component 242 by, in an exemplary embodiment, outputting a signal to focus unit 323, and thus signal processing unit 226, via signal line 322. In an exemplary embodiment, the generated parameter is an output voltage that is used by focus unit 323 to adjust the focus of the sound capture apparatus 310 through beamforming (discussed further below). In an exemplary embodiment, the focus unit 323 and/or the signal processing unit 226 includes an algorithm stored therein that adjusts the direction based on a voltage output by the determinator 320. In an alternate embodiment, the determinator 320 generates a parameter indicative of the rotational orientation of the external component 242, and thus the microphones 224A, 224B and 224C, by outputting a digital signal to focusing unit 323 and/or the signal processing unit 226 that contains the angle relative to the direction of gravity that reference line 550, or another appropriate reference line, to which the alignment of the determinator 320 is known, is positioned (described further below). Any device, system or method that will permit an orientation of the external component/the sound capture apparatus relative to a fixed reference e.g., the direction of gravity) to be ascertained may be used in some embodiments of the present invention.

As noted above, an accelerometer may be used as or part of the determinator 320. In an exemplary embodiment, the accelerometer is fixed relative to the external component 242, and thus microphones 224A, 224B and 2240, such that its orientation relative to, for example, a reference line such as reference line 550, is known. Because the orientation of the microphones 224A, 224B and 224C relative to the reference line 550 is also known (indeed, the reference line 550 is established based on the orientation of the microphones in the embodiments of FIGS. 5-6B), the sound capture apparatus 310 may be focused accordingly. By way of example, FIG. 6A depicts the external component 242 at a rotational orientation such that reference line 550 is at a zero degree angle with the direction of gravity 520. In contrast, FIG. 6B depicts the external component 242 at a rotational orientation such that reference line 550 is at a 165 degree angle with the direction of gravity 520 (with reference line 550' corresponding to the location of reference line 550 as oriented in FIG. 6A), where the sound capture apparatus 310 has directed the focus of the sound capture apparatus as shown by focus area 540.

While the above embodiments have been described in terms of utilizing the direction of gravity as the reference, in an alternate embodiment, a magnetic field generated by the implantable component 244A may be used as the reference, a reference that is fixed to an orientation of the recipient. By way of example, implantable component 244A may be configured such that it produces a magnetic field (field 360 with reference to FIG. 3) that is at least substantially fixed relative to the recipient's head and that may be sensed by the external component 242. In an exemplary embodiment, the magnetic field has a property, such as a fixed pattern and/or direction that can be analyzed by determinator 320 to determine the rotational orientation of the external component 242 relative to the magnetic field. By analogy, such a magnetic field may be akin to the Earth's magnetic field, and the determinator 320 may be akin to a magnetic compass.

It is noted that in an alternate embodiment, the external component may be configured such that it produces the magnetic field and the implantable component 244A may be configured such that it detects the magnetic field. In such an embodiment, the magnetic field varies, relative to the implantable component, with variation in orientation of the external component relative to the implantable component. The implantable component may detect a property of the field and determine from said property an orientation of the external component relative to the implantable component.

In the embodiments just detailed, the component detecting the property of the magnetic field is the component that determines an orientation of the external component based on that property. However, in an alternative embodiment, the component detecting the property of the magnetic field may simply relay data indicative of the detected magnetic field to the other component so that the other component may determine the orientation of the external component.

While the above embodiments have been detailed in terms of utilizing properties of a magnetic field to determine the orientation of the external component 242, other embodiments may use other physical phenomena. By way of example only and not by way of limitation, an electromagnetic signal may be used that has varying properties about the component generating the electromagnetic signal. For example, the varying property may be a signal strength that may be at a first level at a direction of, for example, 45 degrees from a reference on the component at a given distance from the component, and may be a different level at a direction of, for example, 95 degrees from the reference at the given distance. That is, the levels may be detectably different at various angles relative to the reference, and thus the orientation may be determined based on those levels. That is, the hearing prosthesis may be configured to analyze the signal strength and determine an orientation of the external component 242 based on the signal strength. In an exemplary embodiment, the physical phenomenon utilized may be the same as or otherwise based on the principle of the Variable Omni-directional Rangefinder (VOR) utilized in aviation, where an RF signal is generated by one component and is received by another component, and analyzed by one of the components to determine orientation relative to the other component.

In an exemplary embodiment, any device, system or method may be used to practice some or all of the embodiments detailed herein and variations thereof utilizing the aforementioned physical phenomenon (magnetic field, RF signal, etc., herein collectively referred to as a reference field) generated by one or more components of the hearing prosthesis, regardless of which component generates the physical phenomenon, which component detects the physical phenomenon, or which component determines the orientation of the external component.

In yet another alternate embodiment, a gyroscope is or is part of the determinator 320. In yet another alternate embodiment, a gravity biased pendulum may be used as or part of the determinator 320. Any type of angle sensing device may be utilized. Moreover, a miniaturized inertial navigation system or a subset thereof may be used in some embodiments. Any device system or method to generate a parameter indicative of the rotational orientation of the external component relative to a fixed reference may be used in some embodiments of the present invention.

With respect to embodiments utilizing the direction of gravity as the fixed reference, some embodiments may include a feature that compensates for the fact that the recipient will tilt his or her head, and thus change the orientation of the external component 242 relative to the direction of gravity 520. For example, the external component 242 may be configured to recognize a pattern of angle changes and identify when the recipient positions his or head approximately level to the horizon. By way of example, with respect to the embodiment detailed above utilizing the accelerometer that outputs a digital signal that contains the angle relative to the direction of gravity that reference line 550 is positioned, the outputted signal will register a first angle when the recipient's head is level, and a second angle when the recipient's head is tilted downward. The external component may be configured to evaluate the pattern of angles to identify when the recipient is tilting his head downward or holding his head level. The angles corresponding to when the recipient is deter to be tilting his head may be automatically disregarded. In an alternate embodiment, the external component 242 may be configured to ignore intermittent changes in orientation of the external component 242 relative to the direction of gravity 520. Still further by example, an algorithm might be used based on the principal that a recipient will typically tilt his head downward (e.g., to read) more often than he will tilt his head upward and/or the angle that a recipient may tilt his head downward may be relatively uniform as compared to the angle that the recipient tilts his head upward. Registered angles falling within the two extremes may be, most likely, those where the recipient is holding his head level, and thus the external component 242 uses these angles as the basis to adjust the focus of the sound capture apparatus 310. Any device, system or method that may be used to compensate for the fact that the recipient will tilt his head may be used in some embodiments if such will permit embodiments of the present invention to be practiced.

As noted above, the sound capture apparatus 310 is configured to focus on an area (i.e., it includes directional capability) relative to the recipient and the hearing prosthesis 300, via the focus unit 323, is configured to adjust the direction of focus of the sound capture apparatus 310 based on at least a generated parameter indicative of the rotational orientation of the external component 242 relative to a fixed reference. In an exemplary embodiment, the focus of the sound capture apparatus 310 is adjusted through beamforming. In an exemplary embodiment, the sound processing unit 226 receives respective signals from the microphones 224A, 224B and 224C and/or other microphones indicative of sound captured by these microphones. The sound processing unit 226, via focus unit 323, further receives input from the determinator 320 indicative of the generated rotational orientation of the external component. The sound processing unit 226 processes these signals under the direction of the focus unit 323 to adjust the focus of the sound capture apparatus 310 based on the received input from the determinator 320 to adjust the focus of the sound capture apparatus 310. This permits the sound capture apparatus 310 to focus on the area in front of the recipient.

In some embodiments, where the sound processing unit 226 is located in the internal component 244A, the output from focus unit 323 and/or from microphones 224A-C and/or from determinator 320 may be transmitted across link 342 to the internal component 244A where it is received by the sound processing unit 226. In such an exemplary embodiment, the output from focus unit 323 might include instructions to the sound processing unit 226 as to how to process the signals from the microphones to achieve the focusing as detailed herein. In some embodiments, the focus unit 323 may be located in the internal component 244A as well. Accordingly, in an exemplary embodiment, the output from the microphones 224A-C and the determinator 320 may be transmitted across link 342 where it is received by the sound processing unit 226 and/or focus unit 323, which function as detailed above.

As noted above, in some embodiments, the sound processing unit includes focus unit 323 and in other embodiments the focus unit 323 is separate from sound processing unit 226. That is, in some embodiments, a unit separate from the sound processing unit pre-processes the signals from the microphones based on the generated parameter indicative of the rotational orientation of the external component 242 prior to receipt of the now-pre-processed signals by the sound processing unit 226. This unit, such as the focus unit 323, separate from the sound processing unit 226, may variously amplify and/or suppress the respective signals to adjust the focus of the sound capture apparatus 310. In such an exemplary embodiment, signal communication lines 324A, 324B and 324C may lead to focus unit 323 prior to, if at all, leading to sound processing unit 226, as opposed to the configuration depicted in FIG. 3.

In yet another embodiment, one or more of the microphones might be adjusted by the external component 242, via the focus unit 323 and/or sound processing unit 226 and/or the sound capture apparatus 310, to adjust the focus of the sound capture apparatus. In an exemplary embodiment, the external component 242 adjusts the focus of the sound capture apparatus 310 by disabling the microphones furthest from the front of the recipient and enabling the microphone closest to the front of the recipient. With respect to FIGS. 6A and 6B, this may correspond to enabling microphones 224B and 224C, respectively, and disabling the other respective microphones. In an exemplary embodiment, the sound capture apparatus 310 is configured to adjust the focus of the sound capture through selective acceptance and/or disregardance of one or more of the output signals of the microphones. In an exemplary embodiment, the external component 242 adjusts the focus of the sound capture apparatus 310 by disregarding the output of the microphones furthest from the front of the recipient and accepting the output of the microphone closest to the front of the recipient. With respect to FIGS. 6A and 6B, this would correspond to respectively accepting the output signals of microphones 224B and 224C and respectively disregarding the output of the other microphones. In an exemplary embodiment, the sound capture apparatus 310 is configured to adjust the focus of the sound capture through selective maintenance and/or reduction of one or more of the output signals of the microphones. In an exemplary embodiment, the external component 242 adjusts the focus of the sound capture apparatus 310 by reducing the level (or amplitude) of the output of the microphones furthest from the front of the recipient and maintaining the level of the output of the microphone closest to the front of the recipient. With respect to FIGS. 6A and 6B, this would correspond to respectively maintaining the output of microphones 224B and 224C and respectively reducing the output of the other respective microphones. In an exemplary embodiment, the sound capture apparatus 310 is configured to adjust the focus of the sound capture through selective amplification and/or maintenance of one or more of the output signals of the microphones. In an exemplary embodiment, the external component 242 adjusts the focus of the sound capture apparatus 310 by maintaining the level of the output of the microphones furthest from the front of the recipient and increasing the level of the output of the microphone closest to the front of the recipient. With respect to FIGS. 6A and 6B, this would correspond to respectively increasing the output of microphones 224B and 224C and respectively maintaining the output of the other respective microphones.

In yet a further embodiment, one or more of the embodiments described in the preceding paragraph may be combined with one or more of the embodiments detailed herein that utilizes beamforming techniques to focus on a given area. By way of example, and with respect to FIG. 6A, the external component 242 may adjust the focus of the sound capture apparatus 310 by disregarding the output of the microphone 224A, accepting the output of the microphones 224C and 224B and applying beamforming techniques to the output of the microphones 224C and 224B.

Any device, system or method that will permit the focus of the sound capture apparatus to be achieved based on the generated parameter indicative of the rotational orientation of the external component may be used to practice some embodiments of the present invention.

It is noted that while in some embodiments of the present invention the microphones are omnidirectional microphones, other embodiments may be practiced with non-omnidirectional microphones.

In view of the above, some embodiments permit sound capture apparatus 310 to maintain its focus towards a desired area regardless of the rotational orientation of external component 242 relative to the recipient.

An exemplary embodiment includes a method of enhancing hearing of a recipient utilizing a hearing prosthesis. The method entails automatically focusing the sound capture apparatus 310 based on an orientation of a component (e.g., the microphones) of the hearing prosthesis 200 relative to a fixed reference such as the direction of gravity 520. Such a method may include automatically focusing a first focus of the sound capture apparatus 310 in a first direction relative to a frame of reference (e.g., line 550 of FIG. 5A) that is based on the component (e.g., the microphones) of the hearing prosthesis 242 based on a first orientation of the component of the hearing prosthesis relative to the fixed reference. The method further includes automatically focusing a second focus of the sound capture apparatus 310 in a second direction relative to the frame of reference based on the component of the hearing prosthesis based on a second orientation of the external component of the hearing prosthesis relative to the fixed reference, the second orientation being different from the first orientation. FIGS. 6A and 6B schematically illustrate the results of this method. As may be seen in these FIGS., the first focus of the sound capture apparatus and the second focus of the sound capture apparatus, relative to the recipient, are substantially identical, yet the first focus and the second focus are different relative to the frame of reference based on the microphones.

Owing to the use of a magnetic field that permits external component 242 to rotate relative to the recipient, in some embodiments, the external component 242 is attachable to the recipient in potentially an infinite number of rotational orientations relative to the recipient. Accordingly, in at least some exemplary embodiments, external component 242 is attachable to the recipient in at least 36 rotational orientations relative to the recipient that are each at least five and or ten degrees different from their respective neighboring orientations.

While the above embodiments have been detailed in view of focusing on an area in front of the recipient, in other embodiments, the sound capture apparatus 310 may focus on any given area about the user utilizing the devices, systems and methods as detailed herein and variations thereof. By way of example, the external component 242 may include a recipient interface that permits the recipient to control the area of focus of the sound capture apparatus 310. In an exemplary embodiment, the recipient can input a control command to focus on any of twelve positions on a horizontal plane about the recipient (corresponding to the twelve positions of the clock, with the 12 o'clock position being directly in front of the recipient) and/or input a control command to focus on any of twelve positions on a vertical plane about the recipient (corresponding to the twelve positions of the clock, with the 12 o'clock position being directly on top of the recipient). Such embodiments may include an algorithm that processes the received control command and adjusts the focus of the sound capture apparatus 310 based on the spatial orientation of the external component 242 relative to a fixed reference.

FIG. 8 provides a flow-chart 800 for an exemplary algorithm that may be used in some embodiments of the present invention. This algorithm 800 will be described in terms of an exemplary scenario utilizing the external component 242.

In an exemplary scenario, a recipient of a hearing prosthesis (e.g., a direct acoustic cochlear stimulator, cochlear implant, transcutaneous bone conduction devices, etc.) awakens from night sleep and retrieves his or her external component 242 from a charging station remote from the recipient. The recipient had removed the external component 242 from himself/herself the night before and attached it to the charging station to recharge the rechargeable batteries of the external component 242. The user places the external component 242 against his/her head and moves it around over the surface of the skin/hair of his/her head until he/she senses that the magnetic field has been adequately established between the external component 242 and the internal component 244A to hold the external component 242 against his head. The user then releases the external component 242. In this exemplary scenario, the user makes little to no effort to rotationally align the external component 242 in a given manner. The resulting position and alignment of the external component 242/the sound capture apparatus 310 is depicted in FIG. 5. Typically, the spatial position of the external component 242 on the head of the recipient will be the same every time that the recipient attaches the external component 242 to his head, due to the self-aligning properties of the magnetic field that is established between the external component 242 and the internal component 244A. However, the rotational orientation of the external component 242, and thus the sound capture apparatus 310 may be different, as detailed above.

At some point during the actions detailed above in the preceding paragraph, an indication that the rotational orientation of the external component 242 and/or the sound capture apparatus 310 should be evaluated is received by a component of the external component 242 (e.g., a controller (not shown) and/or the sound processing unit 226, etc.). This corresponds to step 810 of algorithm 800. Such indication may be a result of the external component 242 being removed from the charging station, activation of the external component 242 by the recipient and/or sensation of a magnetic field upon placement of the external component 242 adjacent the internal component 244A, etc. Such indication may further be a result of a time period that has elapsed since the last time that the rotational orientation of the external component was evaluated and/or may be a result of the recipient providing a control command to the external component 242 to evaluate the rotational orientation of the external component, etc. (Note that evaluation of the rotational orientation includes reevaluation of the rotational orientation.)

Upon receipt of the indication that the rotational orientation of the external component 242 and/or the sound capture apparatus 310 should be evaluated, a parameter indicative of the rotational orientation of the external component 242 and/or the sound capture apparatus 310 relative to a reference, such as a fixed reference, is generated at step 820. At step 830, a check is (performed to determine if an indication of an alternate direction requirement of the sound capture apparatus 310 has been received. In an exemplary embodiment, the external component 242 is configured to, as a default, focus the sound capture apparatus 320 towards an area corresponding to the front of the recipient, as detailed above. However, an alternate direction requirement of the sound capture apparatus 310 may have been received. Such an exemplary alternate direction requirement may correspond to the recipient inputting that the sound capture apparatus 310 should be focused to the right side of the recipient level with the recipient (3 o'clock position on the horizontal plane, 3 o'clock position on the vertical plane), where the recipient is driving a left side steering wheel automobile and a passenger in the front seat is speaking to the recipient. At step 840, the focus of the sound capture apparatus is adjusted based on the generated parameter indicative of the rotational orientation of the external component and based on any received alternate direction requirement of the sound capture apparatus 310. With respect to the exemplary alternate direction requirement just described, step 840 will result in the sound capture apparatus 310 being focused directly to the right of the recipient level with the recipient's head.

While various embodiments of the present invention have been described above, it should be understood that they have been presented by way of example only, and not limitation. It will be apparent to persons skilled in the relevant art that various changes in form and detail may be made therein without departing from the scope of the invention. Thus, the breadth and scope of the present invention should not be limited by any of the above-described exemplary embodiments, but should be defined only in accordance with the following claims and their equivalents.

What is claimed is:

1. A hearing prosthesis, the hearing prosthesis comprising:
a plurality of sound capture devices, wherein
the hearing prosthesis is configured to generate a parameter indicative of an orientation of the plurality of sound capture devices relative to a reference, and
the hearing prosthesis is configured to adjust a direction of focus of the hearing prosthesis based on at least the parameter.

2. The hearing prosthesis of claim 1, further comprising:
a sound processor configured to process a plurality of signals respectively received from the plurality of sound capture devices to adjust the direction of focus of the hearing prosthesis based on at least the parameter.

3. The hearing prosthesis of claim 1, wherein:
the sound capture devices and component(s) configured to generate the parameter indicative of the orientation are housed in a component of the hearing prosthesis that is external to a recipient of the hearing prosthesis.

4. The hearing prosthesis of claim 1, wherein:
the hearing prosthesis is configured to adjust the direction of focus of the hearing prosthesis based on the orientation of the plurality sound capture devices through selective acceptance and/or disregardance of at least one output signal of a plurality of respective output signals of the plurality of sound capture devices, the output signals being indicative of sound captured by respective sound capture devices of the plurality of sound capture devices.

5. The hearing prosthesis of claim 1, wherein:
the hearing prosthesis is configured to adjust the direction of focus of the hearing prosthesis based on the orientation of the plurality of sound capture devices through at least one of:
selective enablement and/or selective disablement of one or more of the sound capture devices of the plurality of sound capture devices so that at least two sound capture devices are enabled; or
selective acceptance and/or selective disregardance of one or more output signals of a plurality of respective output signals of the plurality of sound capture device such that at least two output signals are accepted; the output signals being indicative of sound captured by respective sound capture devices of the plurality of sound capture devices; and the hearing prosthesis is further configured to adjust the direction of focus of the hearing prosthesis based on the orientation of the plurality of sound capture devices through beamforming, wherein the beamforming includes:
processing output from the at least two sound capture devices that are enabled and/or processing the at least two output signals that are accepted.

6. The hearing prosthesis of claim 1, wherein:
the parameter is based on a direction of gravity.

7. The hearing prosthesis of claim 1, wherein:
the prosthesis includes an accelerometer; and
output from the accelerometer is the parameter indicative of the orientation of the plurality of sound capture devices.

8. The hearing prosthesis of claim 7, wherein:
the accelerometer is configured to output a signal indicative of an orientation of the accelerometer relative to the direction of gravity, wherein the orientation of the accelerometer is fixed relative to the plurality of sound capture devices; and
the outputted signal indicative of an orientation of the accelerometer relative to the direction of gravity is the parameter indicative of the orientation of the plurality of sound capture devices.

9. The hearing prosthesis of claim 1, further comprising:
a gyroscope, wherein the hearing prosthesis is configured to use the gyroscope as the reference.

10. The hearing prosthesis of claim 1, wherein:
the hearing prosthesis is configured to be worn on a side of a recipient's head; and
the hearing prosthesis is configured to account for the possibility that the recipient's head is not consistently aligned with a direction of gravity when adjusting the direction of focus.

11. The hearing prosthesis of claim 1, wherein:
the hearing prosthesis is configured to enable a user thereof to control the direction of focus to be at least a first direction of focus and a second direction of focus substantially different than the first direction of focus.

12. The hearing prosthesis of claim 1, wherein:
the hearing prosthesis is configured to be worn on a head of a recipient of the hearing prosthesis, and the reference exist irrespective of whether the hearing prosthesis is worn on the head of the recipient.

13. The hearing prosthesis of claim 1, wherein:
the hearing prosthesis is a button processor.

14. The hearing prosthesis of claim 1, wherein:
the hearing prosthesis is a unitary component configured to be worn on a side of a head of a human.

15. A method of capturing sound with a hearing prosthesis, comprising:
focusing a sound capture apparatus based on a side of a head of a human that the hearing prosthesis is located, wherein the hearing prosthesis is configured to be worn on either side of the head.

16. The method of claim 15, further comprising automatically focusing the sound capture apparatus based on an orientation of a component of a hearing prosthesis relative to a reference by:
automatically focusing a first focus of the sound capture apparatus in a first direction relative to a frame of reference of the component of the hearing prosthesis based on a first orientation of the component of the hearing prosthesis relative to the reference; and
subsequently automatically focusing a second focus of the sound capture apparatus in a second direction relative to the frame of reference of the component of the hearing prosthesis based on a second orientation of the component of the hearing prosthesis relative to the reference, the second orientation being different from the first orientation.

17. The method of claim 15, further comprising:
evaluating a plurality of generated parameters indicative of a plurality of respective orientations of the component relative to the direction of gravity to identify a parameter of the plurality of parameters that is indicative of a tilt of the recipient's head being normal to the direction of gravity, wherein an orientation of the component of the hearing prosthesis relative to the reference is based on the identified parameter.

18. The method of claim 15, wherein:
the hearing prosthesis includes an implantable component implanted in the recipient, the implantable component configured to impart stimulation directly to an internal body component located internal to the recipient that ultimately results in the evocation of a hearing percept; and
the method further comprises evoking a hearing percept using the implanted component implanted in the recipient by stimulating the internal body component internal to the recipient, the evoked hearing percept based on sound captured by the sound capture apparatus.

19. The method of claim 15, wherein the hearing prosthesis includes a gyroscope, and the reference is the gyroscope.

20. The method of claim 15, further comprising:
placing the hearing prosthesis against a side of a head of the human prior to focusing the sound capture apparatus so that the sound capture apparatus is outside the human, wherein
the action of focusing the sound capture apparatus is executed while the hearing prosthesis is against the side of the head and the sound capture apparatus is outside the human, and
the hearing prosthesis is a unitary component where all sound capture devices of the hearing prosthesis are part of the unitary component.

21. A hearing prosthesis, the hearing prosthesis comprising:
a plurality of sound capture devices, wherein the hearing prosthesis is configured to at least one of:
automatically direct a sound capture direction in a direction relative to a reference irrespective of a rotational orientation of the sound capture devices relative to the reference; or
direct a sound capture direction in a direction irrespective of a side of a head of a human upon which the hearing prosthesis is worn, wherein the hearing prosthesis is configured to be worn on either side of the head.

22. The hearing prosthesis of claim 21, wherein:
the hearing prosthesis is configured to automatically direct the sound capture direction through beamforming.

23. The hearing prosthesis of claim 21, wherein:
the hearing prosthesis is configured to sense an orientation of the plurality of sound capture devices relative to the reference and automatically direct the sound capture direction to encompass the direction relative to the reference irrespective of the rotational orientation of the plurality of sound capture devices relative to the reference based on the sensed orientation.

24. The hearing prosthesis of claim 21, wherein:
the hearing prosthesis includes an accelerometer; and output from the accelerometer is used by the hearing prosthesis to automatically direct the sound capture direction in the direction relative to a reference.

25. The hearing prosthesis of claim 21, wherein the hearing prosthesis is configured to:
   direct a sound capture direction in a direction irrespective of a side of a head of a human upon which the hearing prosthesis is worn, wherein the hearing prosthesis is configured to be worn on either side of the head.

26. The hearing prosthesis of claim 21, wherein:
   the hearing prosthesis is configured to automatically direct a sound capture direction in a direction relative to a reference irrespective of a rotational orientation of the sound capture devices relative to the reference, wherein the hearing prosthesis is configured to be worn on a head of a recipient of the hearing prosthesis, and the reference exist irrespective of whether the hearing prosthesis is worn on the head of the recipient.

* * * * *